US012649707B2

(12) United States Patent
Matsuda et al.

(10) Patent No.: US 12,649,707 B2
(45) Date of Patent: Jun. 9, 2026

(54) METHANOL PRODUCTION METHOD

(71) Applicant: Sumitomo Chemical Company, Limited, Tokyo (JP)

(72) Inventors: Masato Matsuda, Niihama (JP); Tetsuya Suzuta, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 440 days.

(21) Appl. No.: 18/036,262

(22) PCT Filed: Aug. 30, 2021

(86) PCT No.: PCT/JP2021/031684
§ 371 (c)(1),
(2) Date: May 10, 2023

(87) PCT Pub. No.: WO2022/102210
PCT Pub. Date: May 19, 2022

(65) Prior Publication Data
US 2024/0010586 A1 Jan. 11, 2024

(30) Foreign Application Priority Data
Nov. 13, 2020 (JP) ................................. 2020-189765

(51) Int. Cl.
*C07C 29/151* (2006.01)
(52) U.S. Cl.
CPC ................................. *C07C 29/1518* (2013.01)

(58) Field of Classification Search
CPC ..... C07C 29/1518; C07C 5/327; C07C 31/04; C07C 11/04; C07C 11/06; C01B 3/24; C01B 2203/061
See application file for complete search history.

(56) References Cited

U.S. PATENT DOCUMENTS

| | | | |
|---|---|---|---|
| 5,427,762 A | 6/1995 | Steinberg et al. |
| 5,767,165 A | 6/1998 | Steinberg et al. |
| 2008/0269359 A1 | 10/2008 | Bell |

FOREIGN PATENT DOCUMENTS

| | | |
|---|---|---|
| JP | 2005298413 A | 10/2005 |
| JP | 2018008940 A | 1/2018 |
| WO | 9105734 A1 | 5/1991 |
| WO | 2012017893 A1 | 2/2012 |

*Primary Examiner* — Jafar F Parsa
(74) *Attorney, Agent, or Firm* — Panitch Schwarze Belisario & Nadel LLP

(57) ABSTRACT
This method produces methanol with reduced dependency on fossil fuel. The method includes: a gas acquisition step of acquiring a gas (G1) containing hydrogen by a pyrolysis reaction and/or a dehydrogenation reaction of a hydrocarbon; and a conversion step of converting at least part of the gas (G1), and a source gas containing (G2) carbon oxide into methanol. In the conversion step, the reaction is allowed to proceed by condensing a high boiling point component containing converted methanol and water, and discharging the high boiling point component condensed to the outside of the reaction system.

3 Claims, 8 Drawing Sheets

METHANOL PRODUCTION METHOD

CROSS-REFERENCE TO RELATED APPLICATIONS

This application is a Section 371 of International Application No. PCT/JP2021/031684, filed Aug. 30, 2021, which was published in the Japanese language on May 19, 2022 under International Publication No. WO 2022/102210 A1, which claims priority under 35 U.S.C. § 119 (b) to Japanese Application No. 2020-189765, filed Nov. 13, 2020, the disclosures of which are incorporated herein by reference in their entireties.

TECHNICAL FIELD

The present invention relates to a methanol production method.

BACKGROUND ART

In consideration of global environmental problems, a method for producing methanol or dimethyl ether, which is one of the most basic organic substances, by using carbon dioxide recovered from industrial exhaust gas, the atmosphere, or the like, or carbon dioxide obtained by gasification of waste, biomass, or the like, as a raw material has been developed. For example, Patent Document 1 discloses a waste treatment system including a step of synthesizing methanol from hydrogen and carbon dioxide obtained by gasification of waste. On the other hand, Patent Document 2 discloses a method for producing methanol by condensing a product produced using carbon oxide such as carbon dioxide and hydrogen as raw materials.

PRIOR ART DOCUMENTS

Patent Documents

Patent Document 1: WO 2012-017893
Patent Document 2: JP-A-2005-298413

SUMMARY OF THE INVENTION

Problems to be Solved by the Invention

However, one of the problems in the methanol production method using carbon dioxide as a raw material is difficulty in securing hydrogen as another raw material. Hydrogen used as a raw material for general methanol synthesis is industrially often produced by steam reforming of hydrocarbons such as natural gas or petroleum gas. That is, hydrogen produced by the steam reforming is derived from fossil fuel. In consideration of environmental problems, it is required to reduce the dependency on fossil fuel.

An object of one aspect of the present invention is to realize a methanol production method in which the dependency on fossil fuel is reduced.

Means for Solving the Problems

In order to solve the above problems, a methanol production method according to one aspect of the present invention includes: a gas acquisition step of acquiring a gas containing hydrogen by a pyrolysis reaction and/or a dehydrogenation reaction of a hydrocarbon; and a conversion step of converting a source gas containing at least a part of the gas and carbon oxide into methanol, wherein in the conversion step, the reaction is allowed to proceed by condensing a high boiling point component containing converted methanol and water, and discharging the high boiling point component condensed to an outside of a reaction system.

Effect of the Invention

According to one aspect of the present invention, methanol can be produced with reduced dependency on fossil fuel.

MODE FOR CARRYING OUT THE INVENTION

Embodiment 1

Hereinafter, a methanol production method according to an embodiment of the present invention will be described in detail with reference to the drawings together with a production device used for the method. Note that the drawings used below are used to describe the present invention, and may be different from actual dimensions.

The methanol production method according to the present embodiment includes: a gas acquisition step of acquiring a gas containing hydrogen by a pyrolysis reaction and/or dehydrogenation reaction of a hydrocarbon; and a conversion step of converting at least part of the gas and a source gas containing carbon oxide into methanol. The respective steps will be described in detail below.

In the present embodiment, a production system 100 that realizes a methanol production method according to the present embodiment will be described, but the systems described in the present specification and the drawings are merely typical examples, and do not limit the scope of the present invention at all. The same applies to the following other embodiments.

<Methanol Production System>

Figure 1:
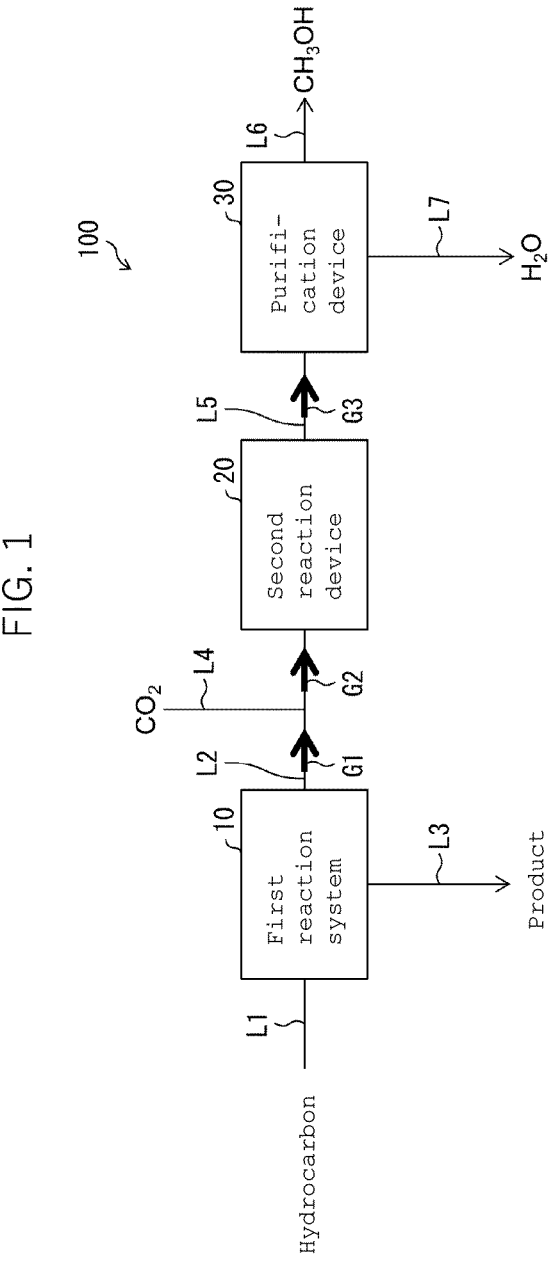
FIG. 1 is a system diagram schematically illustrating a configuration of a production system according to Embodiment 1 of the present invention.

First, an example of a configuration of the production system 100 for realizing a methanol production method according to Embodiment 1 will be described with reference to FIGS. 1 and 2. FIG. 1 is a system diagram schematically illustrating a configuration of the production system 100 according to Embodiment 1.

The production system 100 of the present embodiment is a system that produces methanol from hydrogen obtained by a pyrolysis reaction and/or a dehydrogenation reaction of hydrocarbon, and carbon oxide. In the present specification, the carbon oxide includes at least one of carbon monoxide (CO) and carbon dioxide (CO 2). When the carbon oxide includes both carbon monoxide and carbon dioxide, the abundance for each carbon oxide is not particularly limited. The carbon oxide used as a raw material of the present invention may be, for example, carbon oxide recovered from industrial exhaust gas, the atmosphere or the like, or at least a part of carbon oxide obtained by gasification of waste or biomass.

As illustrated in FIG. 1, the production system 100 of the present embodiment schematically includes a first reaction system 10, a second reaction device 20, a purification device 30, and paths L1 to L7.

A hydrocarbon is supplied from the path L1 to the first reaction system 10. The product obtained in the first reaction system 10 is discharged from the path L3. The path L2 is provided between the first reaction system and the second reaction device 20. A gas G1 containing hydrogen produced as a byproduct by the reaction in the first reaction system 10 is mixed with carbon oxide (for example, carbon dioxide) introduced via the path L4 joined with the path L2, and the mixed gas is supplied to the second reaction device 20 as a source gas G2. The path L5 is provided between the second reaction device 20 and the purification device 30. As a result, a condensate G3 containing methanol and water condensed in the second reaction device 20 is supplied to the purification device Through purification by the purification device 30, methanol is discharged from the path L6, and water is discharged from the path L7. Hereinafter, each device (system) will be described in detail.

The first reaction system 10 is a system for mainly performing a pyrolysis reaction and/or a dehydrogenation reaction of a hydrocarbon. The first reaction system 10 is not required to be configured by a single device. For example, the first reaction system 10 may be a system that includes a reaction device in which pyrolysis and/or dehydrogenation reactions are performed, and associated devices, such as a separation device and/or a recovery device.

In the first reaction system 10, a target product can be obtained by subjecting a hydrocarbon supplied as a raw material to a pyrolysis reaction and/or a dehydrogenation reaction, and at the same time, hydrogen is produced as a byproduct. In the present specification, since the pyrolysis reaction and/or the dehydrogenation reaction of the hydrocarbon by the first reaction system 10 is a reaction involving production of hydrogen, hereinafter, these reactions are collectively referred to as a hydrocarbon dehydrogenation reaction. In the methanol production method of the present invention, hydrogen produced as a byproduct in the first reaction system 10 is used for producing methanol. That is, the first reaction system 10 can be considered to be a system that performs a gas acquisition step of acquiring the gas G1 containing hydrogen by a pyrolysis reaction and/or a dehydrogenation reaction of a hydrocarbon.

Examples of the hydrocarbon dehydrogenation reaction performed by the first reaction system 10 include a reaction (method) for producing olefin. Examples of the olefin production method include a method of producing ethylene by a dehydrogenation reaction of ethane, a method of producing propylene by a dehydrogenation reaction of propane, and a method of producing a lower olefin or the like by a pyrolysis reaction of naphtha. As these olefin production methods, existing methods can be used. As the method, an existing fluidized bed reaction method, a fixed bed reaction method, or the like can be adopted.

Examples of other hydrocarbon dehydrogenation reactions include a method of producing toluene by a dehydrogenation reaction of methylcyclohexane, and a method of producing cyclohexanone by a dehydrogenation reaction of cyclohexanol. In the present invention, hydrogen obtained by the above dehydrogenation reaction is used as a raw material. The type of hydrocarbon as a raw material and a product produced from the hydrocarbon are not particularly limited as long as the reaction for obtaining hydrogen as a raw material is a hydrocarbon dehydrogenation reaction.

Hydrogen produced together with products available for other applications such as production of polyolefins in a hydrocarbon dehydrogenation reaction as described above can be obtained with energy saving, as compared with hydrogen obtained by steam reforming of hydrocarbons, electrolysis of water, or electrolysis of salt water. In addition, in the production system 100, the gas G1 containing hydrogen produced as a byproduct in the first reaction system 10 can be directly supplied to the second reaction device via the path L2. This makes it possible to construct an economical methanol production process.

The second reaction device 20 is a device for performing a conversion step of converting the gas G1 containing hydrogen, and the source gas G2 containing carbon oxide into methanol. FIG. 2 is a cross-sectional view of the second reaction device 20 according to Embodiment 1, taken along a plane perpendicular to the bottom surface of the second reaction device 20. The second reaction device 20 is a chemical reaction device for performing a reaction in which the progress of the reaction in the gas phase is restricted by chemical equilibrium between a raw material and a product containing a component having a boiling point higher than that of the main component of the source gas G2. In other words, the second reaction device 20 is a device capable of proceeding the reaction by condensing a high boiling point component containing the converted methanol and water, and discharging the condensed high boiling point component as the condensate G3 to the outside of the reaction system. The second reaction device 20 illustrated in FIG. 2 is merely an exemplary configuration, and is not limited to the configuration illustrated in FIG. 2.

In the second reaction device 20, the product is condensed and recovered from the reaction vessel, so that the chemical equilibrium is shifted to the product side, and the reaction can proceed. In particular, the second reaction device 20 can be suitably used in the present embodiment in which the source gas G2 contains carbon oxide and hydrogen and the product contains methanol. In the second reaction device 20, chemical reactions represented by the following Formulas (1) and (2) are performed.

$$CO + 2H_2 <=> CH_3OH \tag{1}$$

$$CO_2 + 3H_2 <=> CH_3OH + H_2O \tag{2}$$

Figure 2:
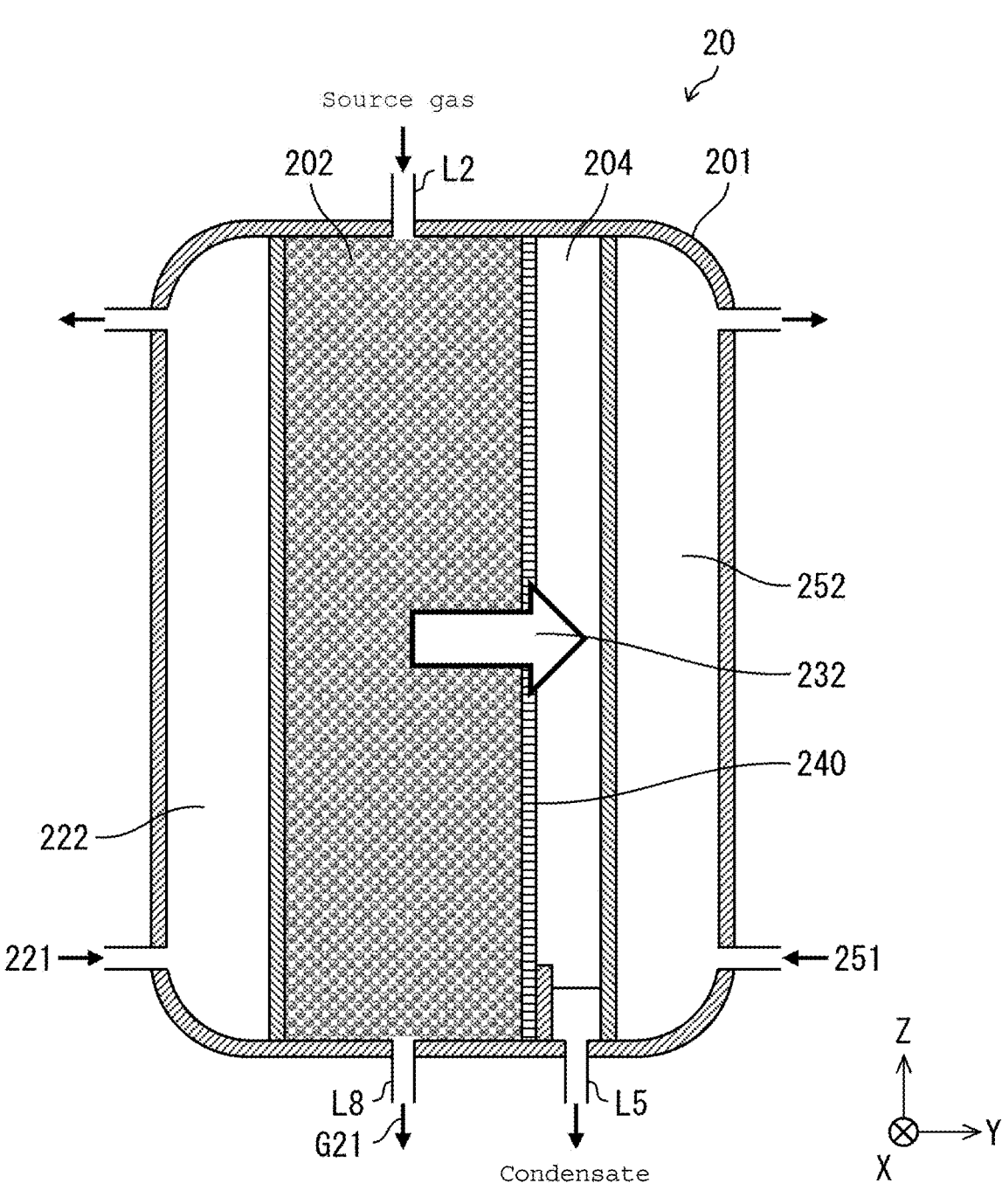
FIG. 2 is a cross-sectional view of a second reaction device according to Embodiment 1 of the present invention, taken along a plane perpendicular to the bottom surface of the second reaction device.

As illustrated in FIG. 2, the second reaction device 20 includes a reaction vessel 201, a first heat exchange part 222, a catalyst layer 202 in contact with the first heat exchange part 222, a permeation wall 240, and a second heat exchange part 252 disposed to be separated from the permeation wall 240 by a space 204. The permeation wall 240 is provided on the catalyst layer 202 on a side opposite to a side where the first heat exchange part 222 is located. The reaction vessel 201 is, for example, a metal container that is made of stainless steel and has pressure resistance.

As illustrated in FIG. 2, the second reaction device 20 may be provided with an exhaust gas discharge path L8. As a result, an unreacted gas G21 can be discharged as exhaust gas. Note that the unreacted gas G21 may be burned after being recovered and before being released as exhaust gas, so that thermal energy generated by the combustion may be used as thermal energy used in the conversion step.

The purification device 30 is a device that performs a purification step of separating water and impurities from the condensate G3, to purify methanol. The condensate G3 obtained from the second reaction device 20 is a liquid mixture containing methanol and water as a product. A method for extracting methanol from the liquid mixture in the purification device 30 is not particularly limited. For example, methanol may be obtained by subjecting the liquid mixture to dehydration and/or purification treatment by a known method to thereby remove water and impurities. Examples of the dehydration purification treatment method include distillation and membrane separation. However, when the purity of methanol is not required, the step of purifying methanol by the purification device 30 may be omitted.

<Steps of Methanol Production Method>

The production method according to Embodiment 1 includes a gas acquisition step and a conversion step. The respective steps will be described in detail below.

(Gas Acquisition Step)

The gas acquisition step is a step of acquiring the gas G1 containing hydrogen by a pyrolysis reaction and/or a dehydrogenation reaction of a hydrocarbon. The gas G1 obtained in the gas acquisition step of the present embodiment can be obtained with energy saving, as compared with hydrogen obtained by steam reforming of hydrocarbons, electrolysis of water, or electrolysis of salt water.

(Conversion Step)

The conversion step is a step of bringing, at least a part of a mixed gas of the gas G1 containing hydrogen, obtained by a hydrocarbon dehydrogenation reaction and carbon oxide, into contact with a catalyst to convert the mixed gas into methanol in a gas phase. In the conversion step, the reaction is proceeded by condensing a high boiling point component containing the converted methanol and water, and discharging the condensed high boiling point component to the outside of the reaction system. As a result, carbon oxide and hydrogen can be converted at an equilibrium conversion rate or more. Here, the equilibrium conversion rate means an equilibrium conversion rate based on at least one of carbon of carbon oxide or hydrogen in the source gas, and is calculated from the equilibrium composition in the gas phase according to the reaction temperature and the pressure.

The conversion step in the second reaction device 20 may be performed in the presence of a so-called inert gas that is not involved in the conversion reaction or the decrease in the activity of the catalyst.

In the present embodiment, a mixed gas obtained by mixing the gas G1 containing hydrogen obtained by a hydrocarbon dehydrogenation reaction with a gas containing carbon oxide can be used as the source gas G2 in the conversion step. In the conversion step, a part or all of carbon monoxide, carbon dioxide, and hydrogen in the source gas G2 can be used. A method for acquiring a gas containing carbon oxide, which can be added, is not particularly limited. For example, carbon oxide obtained when fossil fuel is burned for power generation may be used as the gas containing carbon oxide.

In the present embodiment, as a raw material for producing methanol, hydrogen produced directly from fossil fuel is not used, but hydrogen secondarily obtained by a hydrocarbon dehydrogenation reaction performed for obtaining other products is used. This makes it possible to reduce the dependency on fossil fuel. According to the present embodiment, methanol can be produced more efficiently than the case of using an equilibrium reactor generally used in the production of methanol. Therefore, energy required for the production of methanol can be reduced.

Further, methanol can also be utilized as a raw material for propylene or other olefins by utilizing existing technology such as methanol to propylene (MTP) or methanol to olefin (MTO). Thus, the methanol production method according to the present invention can be used, for example, in a technique for immobilizing carbon oxide such as carbon dioxide released into the atmosphere on olefin and the like. That is, the present invention is an invention that can be expected to contribute to realization of the carbon circulation society.

Embodiment 2

Another embodiment of the present invention will be described below. For convenience of description, members having the same functions as the members described in the above embodiment are denoted by the same reference numerals, and the description thereof will not be repeated.

Figure 3:
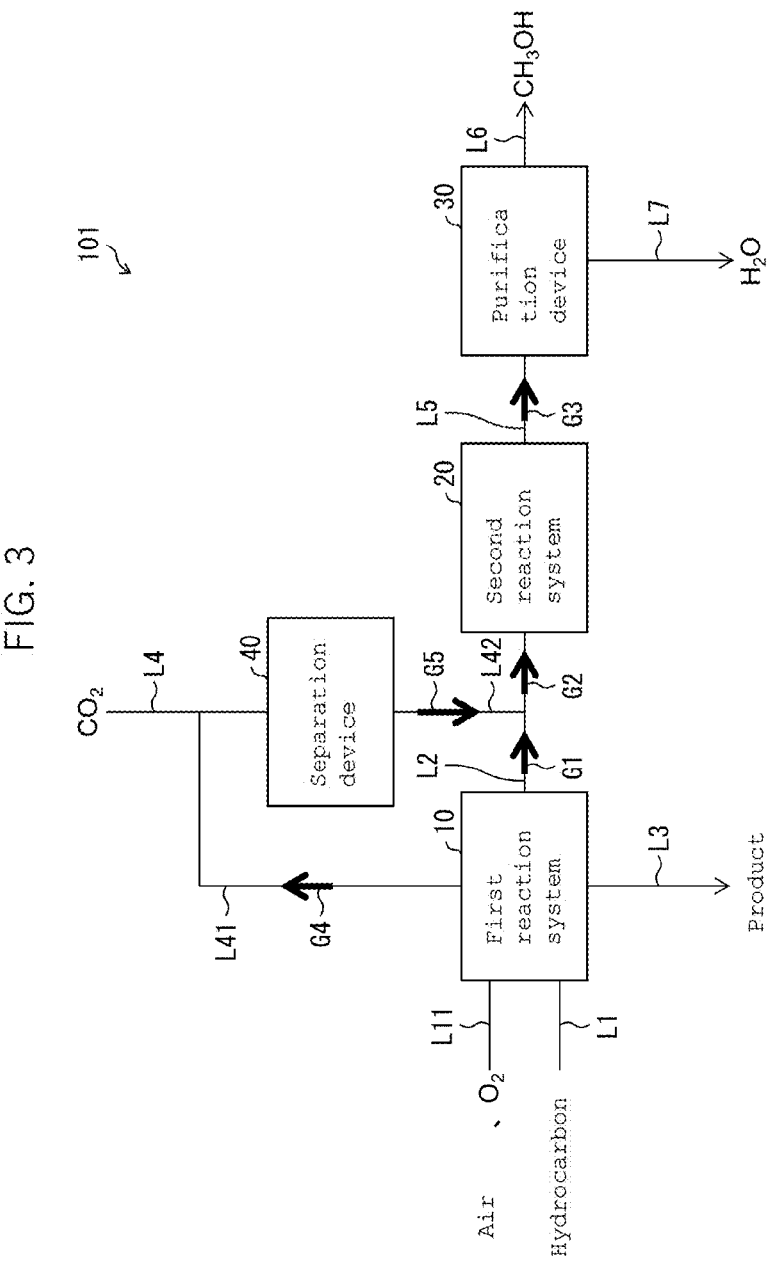
FIG. 3 is a system diagram schematically illustrating a configuration of a production system according to Embodiment 2 of the present invention.

FIG. 3 is a system diagram schematically illustrating a configuration of a production system 101 according to Embodiment 2. The production system 101 is an example of a production system for realizing the methanol production method according to Embodiment 2.

In the methanol production method according to Embodiment 2, at least a part of carbon oxide G4 produced in a hydrocarbon dehydrogenation reaction is used as a raw material for a conversion reaction. Note that the production system 101 illustrated in FIG. 3 is an example, and the present invention is not limited thereto. For example, the step of separating and purifying a gas containing the carbon oxide G4 by a separation device 40 can be omitted.

In the first reaction system 10, a heavy hydrocarbon may be liquefied and discharged, or may be precipitated as a solid and adhere to the catalyst or the inner wall of the reactor. As a countermeasure, an operation is performed in which a gas containing oxygen is supplied from the outside, the heavy hydrocarbon and/or the solid attached to the catalyst or the reactor is partially or completely burned to convert the heavy hydrocarbon or the solid into carbon oxide and/or hydrogen, and the converted gas is released to the outside. That is, in Embodiment 2, in the first reaction system 10, the gas acquisition step and the combustion step of partially or completely burning the byproduct produced in the gas acquisition step are performed.

In Embodiment 2, the carbon oxide G4 obtained in the combustion step is used as a part of the source gas G2 of the conversion reaction in the second reaction device 20. This makes it possible to reduce the amount of carbon oxide released to the environment among carbon oxides produced in the pyrolysis or dehydrogenation reaction of the hydrocarbon. A part or all of the heat generated in the combustion step can also be used as a heat source of the dehydrogenation reaction involving endotherm. Therefore, a process with a low environmental load can be constructed.

In order to realize the production method according to Embodiment 2 described above, the production system 101 of the present embodiment is different from the production system 100 of Embodiment 1 in the following points. As illustrated in FIG. 3, the first reaction system 10 of the production system 101 is provided with a path L11 for supplying air or oxygen (O$_2$) for the combustion step. The production system 101 further includes a path L41, the separation device 40, and a path L42. The carbon oxide G4 discharged from the first reaction system 10 via the path L41 is supplied, together with the carbon oxide introduced via the path L4, to the separation device 40. Carbon oxide G5 after separation and purification, which is discharged from the separation device 40 via the path L42, is supplied to the second reaction device 20 as the source gas G2 together with the gas G1 containing hydrogen generated as a byproduct by the reaction in the first reaction system 10.

In the production system 101, as illustrated in FIG. 3, carbon oxide supplied from the outside of the system may be mixed with the carbon oxide G4 obtained by the hydrocarbon dehydrogenation reaction, and this mixed gas may be used as the carbon oxide G5 supplied to the second reaction device 20. As the carbon oxide supplied from the outside of the system, for example, carbon oxide recovered from another industrial exhaust gas or the atmosphere, or carbon oxide obtained by gasification of waste or biomass can be used.

The separation device 40 is a device that purifies carbon oxide by separation and purification. The carbon oxide G5 as a raw material for the conversion reaction is preferably purified by the separation device 40. That is, the production method of the present embodiment preferably further includes a separation and purification step. The separation and purification method used in the separation device 40 is not limited, and known methods such as an adsorption method, an absorption method, and a membrane separation method can be used. However, the separation and purification step may be omitted by subjecting the carbon oxide G4 discharged from the first reaction system 10 to the conversion reaction in a state where the purity of the carbon oxide G4 is increased by, for example, using pure oxygen instead of air in the combustion step.

In the methanol production method according to Embodiment 2, the hydrocarbon dehydrogenation reaction in the first reaction system 10 is preferably a dehydrogenation reaction of propane.

Hydrogen required for the production of methanol is 2 moles per mole of carbon monoxide (CO) and 3 moles per mole of carbon dioxide (CO$_2$). Therefore, it is ideal that the volume fraction of hydrogen, carbon monoxide, and carbon dioxide in the source gas supplied to the second reaction device 20 is prepared so that the index SN represented by the following Formula (3) is 2. In the following Formula (3), yH$_2$, yCO$_2$, and yCO are volume fractions of hydrogen, carbon dioxide, and carbon monoxide in the source gas supplied to the second reaction device 20, respectively.

$$SN=(yH_2-yCO_2)/(yCO+yCO_2) \qquad (3)$$

The dehydrogenation reaction of propane is particularly preferable because the index SN of the composition ratio between hydrogen produced by the dehydrogenation reaction and carbon oxide obtained through the combustion step is close to 2.

The production method according to the present embodiment further includes the combustion step of burning a byproduct produced in the gas acquisition step, and carbon oxide obtained in the combustion step is used as a part of the source gas.

With the above configuration, the yield of carbon in the hydrocarbon supplied as a raw material can be improved.

Embodiment 3

Another embodiment of the present invention will be described below. For convenience of description, members having the same functions as the members described in the above embodiment are denoted by the same reference numerals, and the description thereof will not be repeated.

Figure 4:
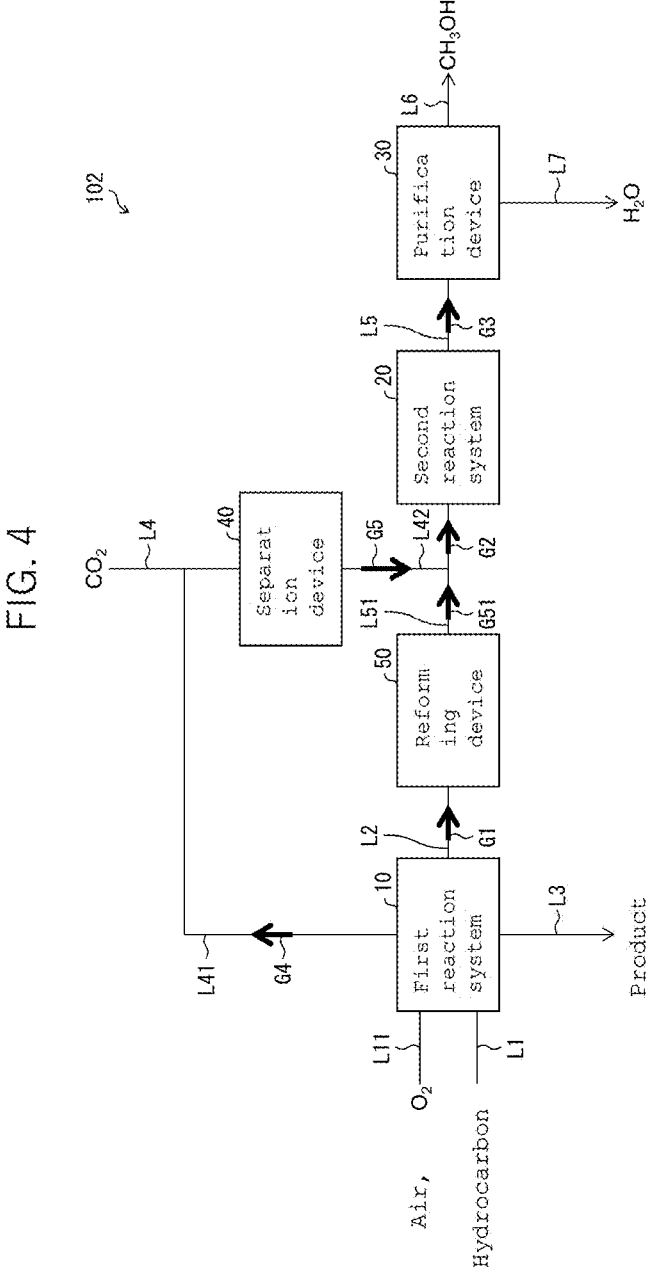
FIG. 4 is a system diagram schematically illustrating a configuration of a production system according to Embodiment 3 of the present invention.

FIG. 4 is a system diagram schematically illustrating a configuration of a production system 102 according to Embodiment 3. The production system 102 is an example of a production system for realizing the methanol production method according to Embodiment 3.

The methanol production method according to Embodiment 3 may further include, between the gas acquisition step and the conversion step, a reforming step of reforming at least a part of a hydrocarbon produced as a byproduct in the gas acquisition step into carbon oxide and/or hydrogen.

In the hydrocarbon dehydrogenation reaction, a low boiling point component (byproduct hydrocarbon) such as methane, ethylene, or ethane is produced as an impurity, in addition to hydrogen. The byproduct hydrocarbon can be contained in the gas G1 discharged from the first reaction system 10. In the reforming step, these byproduct hydrocarbons contained in the gas G1 are converted into carbon oxide and hydrogen by oxidative decomposition or steam reforming. This makes it possible to use the byproduct hydrocarbon as at least a part of the source gas G2 used in the conversion step.

In order to realize the production method according to Embodiment 3 described above, the production system 102 of the present embodiment is different from the production system 101 of Embodiment 2 in the following points. As illustrated in FIG. 4, in the production system 102, a reforming device 50 is provided between the first reaction system 10 and the second reaction device 20. The path L2 is provided between the first reaction system 10 and the reforming device 50. The gas G1 containing hydrogen produced as a byproduct in the first reaction system 10 is supplied to the reforming device 50 via the path L2. A gas G51 reformed by the reforming device 50 is discharged from the reforming device 50 via a path L51, and is supplied to the second reaction device 20 as the source gas G2 together with the carbon oxide G5 separated and purified by the separation device 40. Note that the production system 102 illustrated in FIG. 4 is an example, and the present invention is not limited thereto. For example, the reforming device 50 may be moved to a path after mixing the gas G51 and the carbon oxide G5.

The reforming device 50 is a device that converts the hydrocarbon produced as a byproduct in first reaction system 10 into carbon oxide and hydrogen by oxidative decomposition or steam reforming. The method for oxidative decomposition or steam reforming of the hydrocarbon used in the reforming device 50 is not particularly limited, and known methods such as partial oxidation and autothermal steam reforming can be used.

The production method according to the present embodiment further includes, between the gas acquisition step and the conversion step, a reforming step of reforming at least a part of a hydrocarbon produced as a byproduct in the gas acquisition step into carbon oxide and/or hydrogen.

Use of the present embodiment can further improve the yield of carbon in the hydrocarbon supplied as a raw material.

EXAMPLES

Example 1

Figure 5:
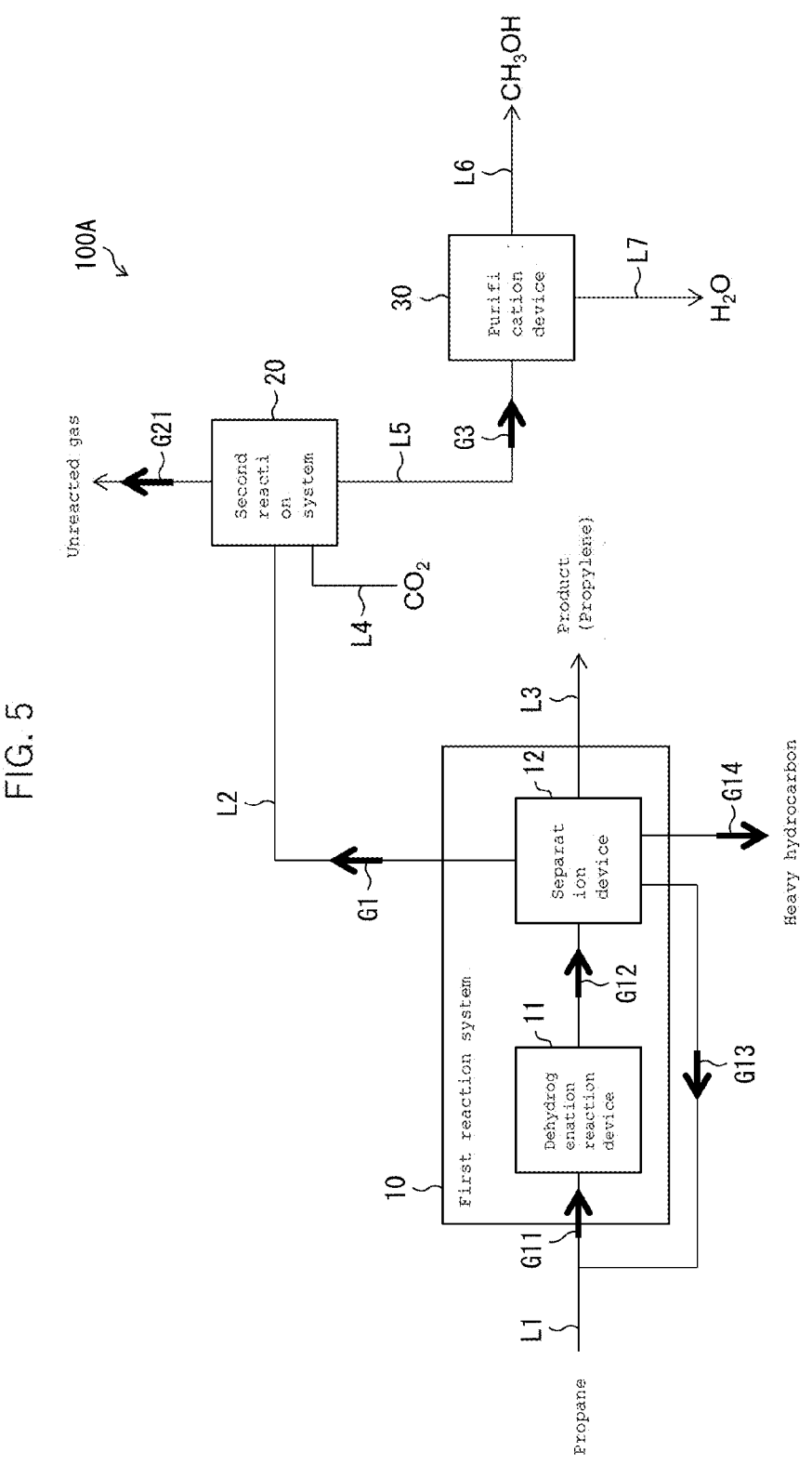
FIG. 5 is a system diagram schematically illustrating a configuration of a production system according to Example 1 of the present invention.

In the present example, a specific example of the above production system 100 will be described. Note that members having the same functions as the members described in the above embodiment are denoted by the same reference numerals, and the description thereof will not be repeated. The same applies to other examples. FIG. 5 is a system diagram schematically illustrating a configuration of a production system 100A according to Example 1. The production system 100A is a system that produces methanol from hydrogen obtained by a dehydrogenation reaction of propane and carbon dioxide supplied from the outside of the system.

As illustrated in FIG. 5, the production system 100A schematically includes the first reaction system 10, the second reaction device 20, the purification device 30, and the paths L1 to L7. The first reaction system 10 of the present example includes a dehydrogenation reaction device 11 and a separation device 12.

Propane supplied from the path L1 is mixed with unreacted propane G13 separated by the separation device 12, and the mixed gas is supplied to the dehydrogenation reaction device 11 as a mixed gas G11. A mixed gas G12 containing propylene and hydrogen is obtained by dehydrogenating propane in the dehydrogenation reaction device 11.

The mixed gas G12 is supplied to the separation device 12, and is separated into crude hydrogen (gas G1 containing hydrogen) containing light hydrocarbons such as propylene and methane, the unreacted propane G13, and a heavy hydrocarbon G14 containing a precipitate (separation step). Among these separated substances, propylene is discharged as a product from the path L3. The gas G1 containing hydrogen is supplied as a source gas to the second reaction device 20 via the path L2. Carbon dioxide as an additional source gas is supplied to the second reaction device 20 via the path L4 so that the index SN calculated by the above Formula (3) is 2 in the source gas supplied to the second reaction device 20.

In the second reaction device 20, the gas G1 and the supplied carbon oxide are reacted in a gas phase to be converted into methanol and water (conversion step). In the conversion step, the produced methanol and water are sequentially condensed and separated from the gas phase portion to promote the progress of the reaction. The unreacted gas G21 is removed to the outside of the system.

The condensate G3 containing methanol and water condensed in the second reaction device 20 is supplied to the purification device 30 via the path L5. In the purification device 30, methanol and water are separated, and methanol is discharged from the path L6 and water is discharged from the path L7.

According to the present example, 61% of hydrogen generated in the dehydrogenation reaction device 11 is used as hydrogen in methanol. Further, according to the present example, 1.07 mol of carbon atoms per mol of methanol are discharged to the outside of the system. The carbon atoms to be discharged are derived from the heavy hydrocarbon G14 discharged from the separation device 12 and the unreacted gas G21 discharged from the second reaction device 20.

Example 2

Figure 6:
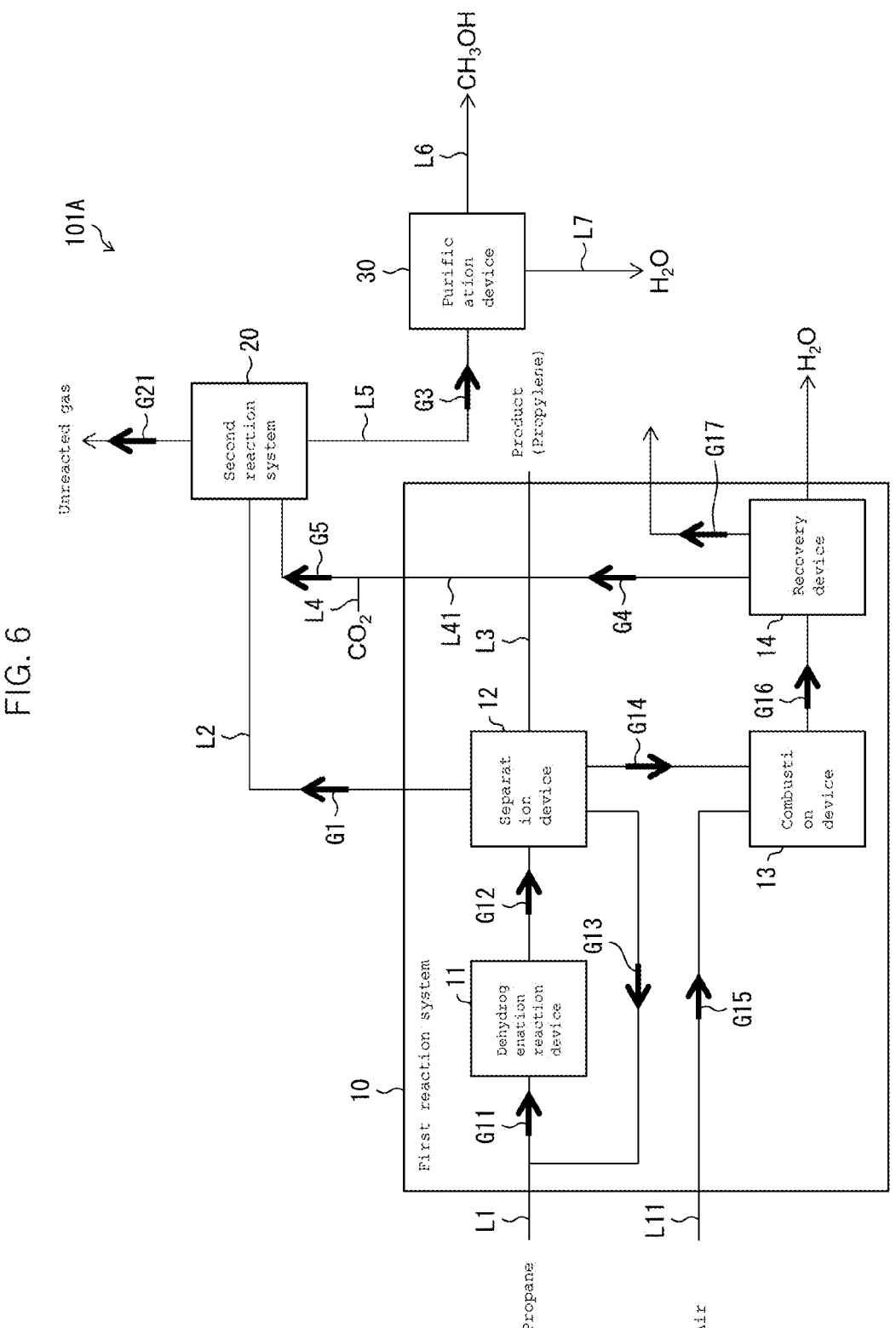
FIG. 6 is a system diagram schematically illustrating a configuration of a production system according to Example 2 of the present invention.

In the present example, a specific example of the above production system 101 will be described. FIG. 6 is a system diagram schematically illustrating a configuration of a production system 101A according to Example 2. The production system 101A is a system that produces methanol from hydrogen obtained by a dehydrogenation reaction of propane, and carbon oxide containing carbon dioxide generated in the combustion step.

As illustrated in FIG. 6, the production system 101A schematically includes the first reaction system 10, the second reaction device 20, the purification device 30, and the paths L1 to L7. The separation device 40 is not included in the production system 101A. The first reaction system 10 of the present example includes the dehydrogenation reaction device 11, the separation device 12, a combustion device 13, and a recovery device 14.

Propane supplied from the path L1 is mixed with the unreacted propane G13 separated by the separation device 12, and the mixed gas is supplied to the dehydrogenation reaction device 11 as the mixed gas G11. The mixed gas G12 containing propylene and hydrogen is obtained by dehydrogenating propane in the dehydrogenation reaction device 11.

The mixed gas G12 is supplied to the separation device 12, and is separated into crude hydrogen (gas G1 containing hydrogen) containing light hydrocarbons such as propylene and methane, the unreacted propane G13, and the heavy hydrocarbon G14 containing a precipitate (separation step). Among these separated substances, propylene is discharged as a product from the path L3. The gas G1 containing hydrogen is supplied as a source gas to the second reaction device 20 via the path L2.

The heavy hydrocarbon G14 containing a precipitate is supplied to the combustion device 13 and burned by air G15 supplied via the path L11. As a result, a mixture G16 of carbon dioxide, water, and nitrogen is obtained. The mixture G16 is supplied to the recovery device 14 and separated into the carbon oxide G4, a gas G17 mainly composed of nitrogen, and water.

The recovered carbon oxide G4 is mixed with carbon dioxide for adjustment, which is supplied from the outside of the system via the path L4, and the mixed gas is supplied to the second reaction device 20. A mixture of the carbon oxide G4 and the carbon dioxide for adjustment is referred to as carbon oxide G5. At this time, carbon dioxide for adjustment is supplied so that the index SN calculated from the carbon oxide molar volume of the carbon oxide G5 and the molar volume of hydrogen in the gas G1, using the above Formula (3) is 2.

In the second reaction device 20, similarly to Example 1, the gas G1 containing hydrogen and the supplied carbon dioxide (carbon oxide G5) are reacted in a gas phase to be converted into methanol and water (conversion step). The unreacted gas G21 is removed to the outside of the system.

The condensate G3 containing methanol and water condensed in the second reaction device 20 is supplied to the purification device 30 via the path L5. In the purification device 30, methanol and water are separated, and methanol is discharged from the path L6 and water is discharged from the path L7.

According to the present example, 61% of hydrogen generated in the dehydrogenation reaction device 11 is used as hydrogen in methanol. Further, according to the present example, 0.59 mol of carbon atoms per mol of methanol are discharged to the outside of the system. The carbon atoms to be discharged are derived from the unreacted gas G21 discharged from the second reaction device 20.

Example 3

Another example of the present invention will be described below.

Figure 7:
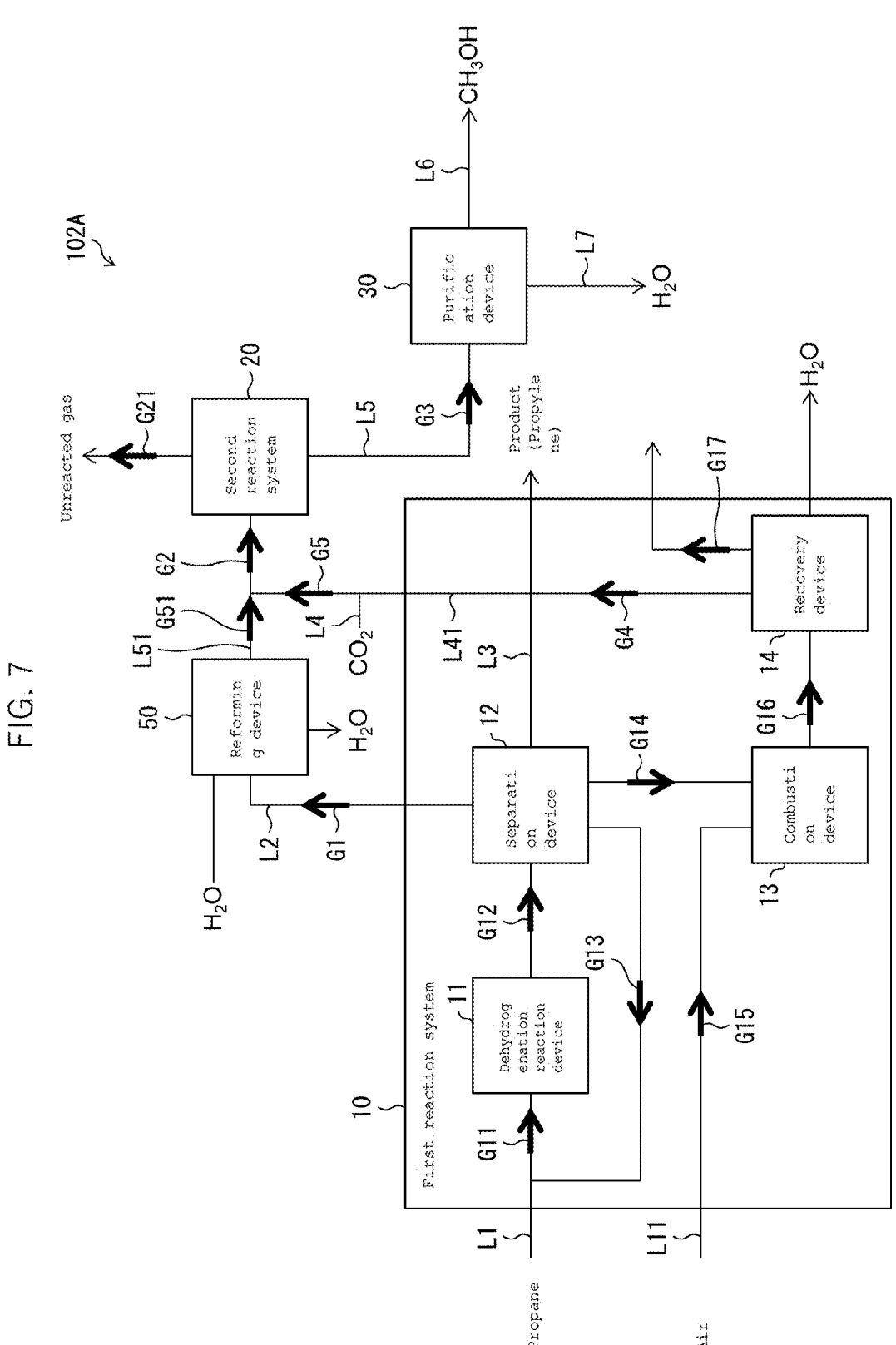
FIG. 7 is a system diagram schematically illustrating a configuration of a production system according to Example 3 of the present invention.

In the present example, a specific example of the above production system 102 will be described. FIG. 7 is a system diagram schematically illustrating a configuration of a production system 102A according to Example 3. Similarly to the production system 101A of Example 2, the production system 102A is a system that produces methanol from hydrogen obtained by a dehydrogenation reaction of propane, and carbon dioxide containing carbon dioxide generated in the combustion step. The production system 102A is different from the production system 101A in that the reforming device 50 is provided between the first reaction system 10 and the second reaction device 20.

As illustrated in FIG. 7, the production system 102A schematically includes the first reaction system 10, the reforming device 50, the second reaction device 20, the purification device 30, and the paths L1 to L7. The separation device 40 is not included in the production system 102A. The first reaction system 10 of the present example includes the dehydrogenation reaction device 11, the separation device 12, the combustion device 13, and the recovery device 14.

Propane supplied from the path L1 is mixed with the unreacted propane G13 separated by the separation device 12, and the mixed gas is supplied to the dehydrogenation reaction device 11 as the mixed gas G11. The mixed gas G12 containing propylene and hydrogen is obtained by dehydrogenating propane in the dehydrogenation reaction device 11.

The mixed gas G12 is supplied to the separation device 12, and is separated into crude hydrogen (gas G1 containing hydrogen) containing light hydrocarbons such as propylene and methane, the unreacted propane G13, and the heavy hydrocarbon G14 containing a precipitate (separation step). Among these separated substances, propylene is discharged as a product from the path L3. The gas G1 containing hydrogen is supplied to the reforming device 50 via the path L2.

The heavy hydrocarbon G14 containing a precipitate is supplied to the combustion device 13 and burned by the air G15 supplied via the path L11. As a result, the mixture G16 of carbon oxide, water, and nitrogen is obtained. The mixture G16 is supplied to the recovery device 14 and separated into the carbon oxide G4, the gas G17 mainly composed of nitrogen, and water.

The recovered carbon oxide G4 is mixed with carbon dioxide for adjustment, which is supplied from the outside of the system via the path L4. A mixture of the carbon oxide G4 and the carbon dioxide for adjustment is referred to as the carbon oxide G5.

Water having a number of moles that is twice the number of moles of carbon of the light hydrocarbon contained in the gas G1 is supplied to the reforming device from the outside of the system. In the reforming device water supplied from the outside of the system and the gas G1 are reacted in a gas phase to convert the light hydrocarbon contained in the gas G1 into carbon monoxide, carbon dioxide, and water. The unreacted water is discharged to the outside of the system. The unreacted water is separated, the gas G51 discharged via the path L51 is mixed with the carbon oxide G5, and the mixed gas is supplied to the second reaction device 20 as the source gas G2.

At this time, carbon dioxide for adjustment is supplied so that the index SN defined by the above Formula (3) is close to 2 in the volume fraction of hydrogen, carbon monoxide, and carbon dioxide in the source gas G2.

In the second reaction device 20, similarly to the above examples, the gas G51 (gas containing hydrogen) and carbon oxide (carbon oxide G5) are reacted in a gas phase to be converted into methanol and water (conversion step). The unreacted gas G21 is removed to the outside of the system.

The condensate G3 containing methanol and water condensed in the second reaction device 20 is supplied to the purification device 30 via the path L5. In the purification device 30, methanol and water are separated, and methanol is discharged from the path L6 and water is discharged from the path L7.

According to the present example, 71% of hydrogen generated in the dehydrogenation reaction device 11 is used as hydrogen in methanol. Further, according to the present example, 0.05 mol of carbon atoms per mol of methanol are discharged to the outside of the system. The carbon atoms to be discharged are derived from the unreacted gas G21 discharged from the second reaction device 20.

COMPARATIVE EXAMPLE

Hereinafter, a comparative example will be described below.

Figure 8:
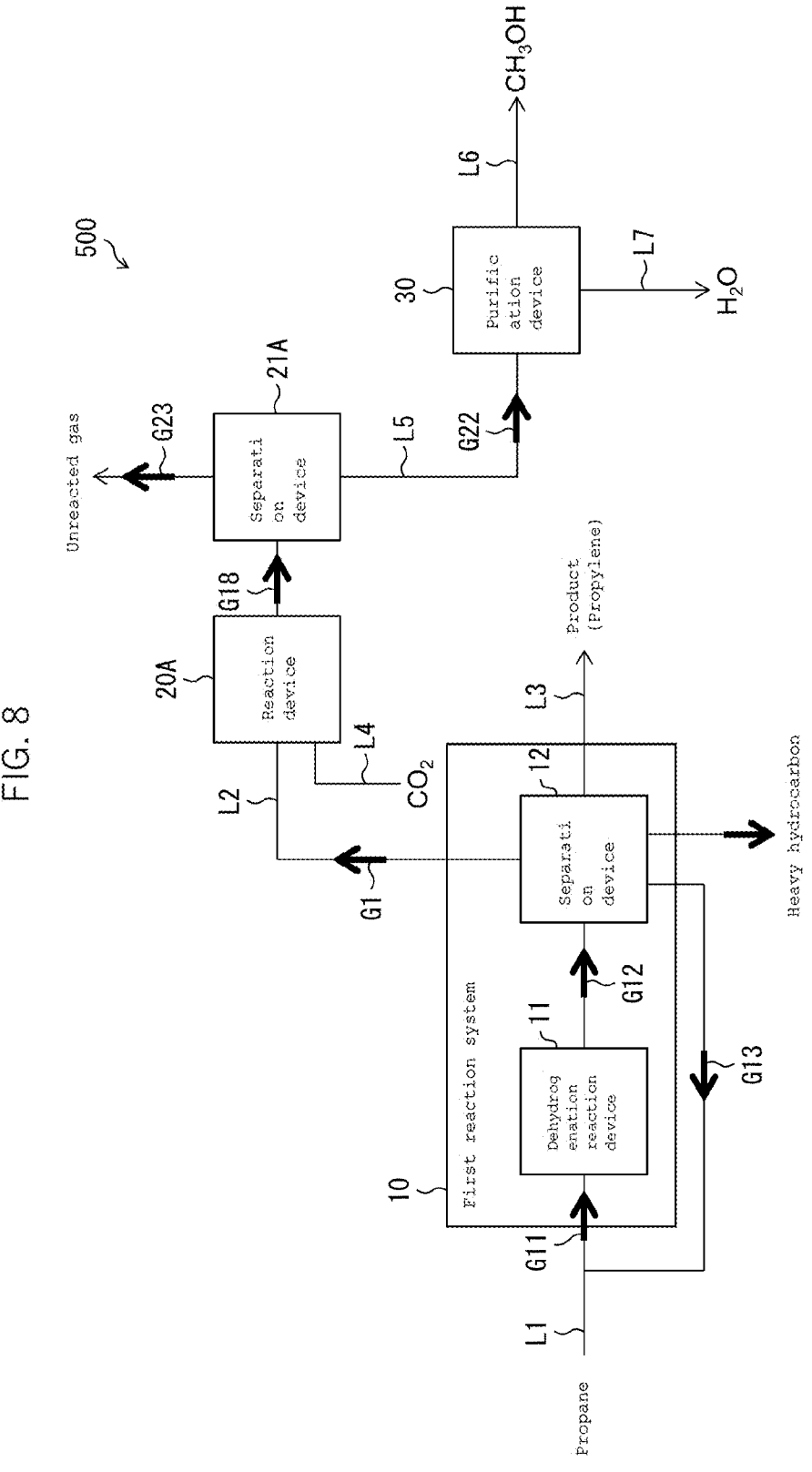
FIG. 8 is a system diagram schematically illustrating a configuration of a production system according to a comparative example.

In the present comparative example, a specific example of a production system 500 which is out of the scope of the present invention will be described. FIG. 8 is a system diagram schematically illustrating a configuration of the production system 500 according to the comparative example.

The production system 500 is different from the production system 100A of Example 1 in that the production system 500 includes a reaction device 20A and a separation device 21A which are out of the scope of the present invention instead of the second reaction device 20 which is within the scope of the present invention. More specifically, the reaction device 20A is a reaction device that performs a conversion reaction of methanol, but is not an internal condensation type reaction device that condenses a high boiling point component containing converted methanol and water and outputs the condensed high boiling point component to the outside of the reaction system. Other configurations are similar to those of the production system 100A of Example 1.

Similarly to Example 1, crude hydrogen (gas G1 containing hydrogen) discharged from the separation device 12 is supplied as a source gas to the reaction device 20A via the path L2. Additional carbon dioxide is supplied to the reaction device 20A via the path L4 so that the index SN calculated by the above Formula (3) is 2 in the source gas supplied to the reaction device 20A.

In the reaction device 20A, the gas G1 and the supplied carbon dioxide are reacted in a gas phase to be converted into methanol and water. The produced methanol and water are supplied as a gas mixture G18 together with the unreacted substances, to the separation device 21A. In the separation device 21A, the gas mixture G18 is separated into the unreacted gas G21 and the condensate G22 by a gas-liquid separation operation. The unreacted gas G21 is removed to the outside of the system. The condensate G22 is supplied to the purification device 30 via the path L5. In the purification device 30, methanol and water are separated, and methanol is discharged from the path L6 and water is discharged from the path L7.

According to the present comparative example, 17% of hydrogen generated in the dehydrogenation reaction device 11 is used as hydrogen in methanol. Further, according to the present comparative example, 6.51 mol of carbon atoms per mol of methanol are discharged to the outside of the system. The carbon atoms to be discharged are derived from the heavy hydrocarbon discharged from the separation device 12 and the unreacted gas G21 discharged from the separation device 21A.

SUMMARY OF EXAMPLES

From the above results, the amount of discharge of carbon atoms per mol of methanol was 6.51 mol in the comparative example which is out of the scope of the present invention, whereas the amount of discharge was 1.07 mol in Example 1 which is within the scope of the present invention. The above results demonstrated that the amount of discharge of carbon atoms per mol of methanol was greatly reduced by the present invention. This means that the yield of carbon in the hydrocarbon supplied as a raw material is improved by the present invention. The results demonstrated that methanol was efficiently produced by the present invention.

The amount of discharge of carbon atoms per mol of methanol in Example 2 was 0.59 mol. This result demonstrated that the yield of carbon in the hydrocarbon supplied as a raw material was further improved by adding the combustion step.

Further, the amount of discharge of carbon atoms per mol of methanol in Example 3 was 0.05 mol. This result demonstrated that the yield of carbon in the hydrocarbon supplied as a raw material was further improved by adding the reforming step.

DESCRIPTION OF REFERENCE SIGNS

100, 100A, 101, 101A, 102, 102A Production system
10 First reaction system
20 Second reaction device
30 Purification device
40 Separation device
50 Reforming device
G1 Gas (gas containing hydrogen)
G2 Source gas
G3 Condensate
G4 Carbon oxide
FIG. 1
10 First reaction system
20 Second reaction device
30 Purification device
1 Hydrocarbon
2 Product
FIG. 2
1 Source gas
2 Condensate
FIG. 3
10 First reaction system
20 Second reaction device
30 Purification device
40 Separation device
1 Air
2 Hydrocarbon
3 Product
FIG. 4

10 First reaction system
20 Second reaction device
30 Purification device
40 Separation device
50 Reforming device
1 Air
2 Hydrocarbon
3 Product
FIG. 5
10 First reaction system
11 Dehydrogenation reaction device
12 Separation device
20 Second reaction device
30 Purification device
1 Propane
2 Heavy hydrocarbon
3 Product (propylene)
4 Unreacted gas
FIG. 6
10 First reaction system
11 Dehydrogenation reaction device
12 Separation device
13 Combustion device
14 Recovery device
20 Second reaction device
30 Purification device
1 Propane
2 Air
3 Product (propylene)
4 Unreacted gas
FIG. 7
10 First reaction system
11 Dehydrogenation reaction device
12 Separation device
13 Combustion device
14 Recovery device
20 Second reaction device
30 Purification device
50 Reforming device
1 Propane
2 Air
3 Product (propylene)
4 Unreacted gas
FIG. 8
10 First reaction system
11 Dehydrogenation reaction device
12 Separation device
20A Reaction device
21A Separation device
30 Purification device
1 Propane
2 Heavy hydrocarbon
3 Product (propylene)
4 Unreacted gas

The invention claimed is:
1. A methanol production method, comprising:
a gas acquisition step of acquiring a gas containing hydrogen by a pyrolysis reaction and/or a dehydrogenation reaction of a hydrocarbon; and
a conversion step of converting a source gas containing at least a part of the gas and carbon oxide into methanol, wherein
in the conversion step, the reaction is allowed to proceed by condensing a high boiling point component containing converted methanol and water, and discharging the high boiling point component condensed to an outside of a reaction system, and the method further comprises a combustion step of burning a byproduct produced in the gas acquisition step, wherein carbon oxide obtained in the combustion step is used as a part of the source gas.

2. The methanol production method according to claim 1, wherein the gas acquisition step includes a dehydrogenation reaction of propane.

3. The methanol production method according to claim 1, further comprising, between the gas acquisition step and the conversion step, a reforming step of reforming at least a part of a hydrocarbon produced as a byproduct in the gas acquisition step into carbon oxide and/or hydrogen.

\* \* \* \* \*